United States Patent [19]

Ziegenhorn et al.

[11] Patent Number: 5,407,836
[45] Date of Patent: Apr. 18, 1995

[54] PROCESS AND REAGENT FOR THE DETERMINATION OF LOW DENSITY LIPOPROTEINS (LDL)

[75] Inventors: Joachim Ziegenhorn, Starnberg; Sigbert Schiefer, Pähl; Brigitte Dräger, Tutzing, all of Germany

[73] Assignee: Boehringer Mannheim GmbH, Mannheim-Waldhof, Germany

[21] Appl. No.: 85,456

[22] Filed: Jun. 30, 1993

Related U.S. Application Data

[63] Continuation of Ser. No. 596,757, Oct. 10, 1990, abandoned, which is a continuation of Ser. No. 423,515, Oct. 13, 1989, abandoned, which is a continuation of Ser. No. 484,679, Apr. 13, 1983, abandoned.

[30] Foreign Application Priority Data

Apr. 23, 1982 [DE] Germany ................ 32 15 310.4

[51] Int. Cl.$^6$ ............... G01N 33/539; G01N 33/543; G01N 33/92
[52] U.S. Cl. ................... 436/539; 436/518; 436/541; 436/71; 436/815; 435/7.93; 435/11; 435/962; 530/389.3; 530/391.1
[58] Field of Search ............ 435/7.1, 11, 19, 810, 435/962; 436/539, 547, 13, 71, 175; 530/389.3, 390.5, 419, 391.1

[56] References Cited

U.S. PATENT DOCUMENTS

| | | | |
|---|---|---|---|
| 4,184,921 | 1/1980 | Roeschlau et al. | 435/11 |
| 4,211,530 | 7/1980 | Gouerde et al. | 436/536 |
| 4,399,217 | 8/1983 | Holmquist et al. | 435/7.93 |
| 4,521,519 | 6/1985 | Draeger et al. | 436/17 X |
| 4,544,630 | 10/1985 | Ziegenhorne et al. | 435/11 |

OTHER PUBLICATIONS

Milne, R. W. et al "Characterization of Monoclonal Antibodies against Human Apolipoprotein E", J. Clin. Invest. 68:111-7 1981.

Chajek et al. "Isolation and Characterization of a Human Serum Cholesteryl ester transfer protein" Proc. Natl. Acad Sci 75(7):3445 1978.

Naito, H. in *Clinical Laboratory Annual*, vol. 3 (Eds. H Homberger & J. Batsakis), pp. 271–282, 1984.

Mangold, H. K. et al. Clinical Biochemistry Principles & Methods vol. 11 (Eds. Curtius & Roth) pp. 1009–1017, 1978.

Basic Exercises in Immunochemistry, A Laboratory Manual pp. 1–13, 1969.

*Primary Examiner*—Toni R. Scheiner
*Assistant Examiner*—Nancy J. Parsons
*Attorney, Agent, or Firm*—Felfe & Lynch

[57] ABSTRACT

The present invention provides a process for the determination of low density lipoproteins (LDL) in body fluids, wherein high density lipoprotein (HDL) antibodies are added to a sample to be investigated, insolubles formed are separated off and the LDL or one of its components is determined in the supernatant.

The present invention also provides a reagent for the determination of the LDL fraction in body fluids, wherein it contains HDL antibodies.

16 Claims, No Drawings

PROCESS AND REAGENT FOR THE DETERMINATION OF LOW DENSITY LIPOPROTEINS (LDL)

This application is a continuation of application Ser. No. 07/596,757, filed Oct. 10, 1990, now abandoned, which is a continuation of application Ser. No. 07/423,515, filed Oct. 13, 1989, now abandoned, which is a continuation of Ser. No. 06/484,679, filed Apr. 13, 1983, now abandoned.

The present invention is concerned with a process and a reagent for the determination of low density lipoproteins (LDL).

The determination of the LDL fraction (low density lipoproteins), which is also called the $\beta$-lipoprotein fraction, has achieved considerable importance for the differentiated diagnosis of a lipid metabolism disturbance.

Hypercholesterolaemia and hypertriglyceridaemia favour the formation of atherosclerosis and of heart infarct. Therefore, determinations of cholesterol and triglycerides in serum belong to the most frequently carried out tests in the clinical-chemical routine laboratory.

Numerous investigations of the fat metabolism have come to the conclusion that the individual coronary risk can be better assessed by determining not only the change in the triglyceride and cholesterol level but also the fundamentally pathological displacements in the lipoprotein pattern (Münch. med. Wschr., 121, (1979) 1639).

The known plasma lipoproteins contain a differingly high proportion of protein (apolipoproteins), phospholipids, cholesterol and triglycerides. On the basis of their behaviour (differing density) in an analytical ultracentrifuge and on the basis of their differing migration speeds in gel electrophoresis, they can be subdivided into four different classes:

chylomicrons
pre-$\beta$-lipoprotein=VLDL (very low density lipoprotein)
$\beta$-lipoprotein=LDL (low density lipoprotein)
$\alpha$-lipoprotein=HDL (high density lipoprotein).

The investigation of the function of the lipoproteins showed that LDL, amongst the lipoproteins, represents the decisive atherogenic component, an increase of which in the blood indicates an increased risk of a coronary heart disease. The early recognition and combating of this state is of great importance. Therefore, there is a need for a practical process for the quantitative determination of the LDL concentration in serum and plasma.

Hitherto, for the determination of the LDL cholesterol value, essentially four methods have been used, all of which, however, suffer from certain disadvantages:

1. Ultracentrifugation

This process is not suitable for a routine laboratory because it requires the use of special apparatus and carrying it out requires an extremely careful operating technique and a very high expenditure of time (several days centrifuging) in an ultracentrifuge. Therefore, this analysis process has hitherto been restricted to medical research laboratories.

2. Electrophoretic separation with subsequent visualisation of the lipoprotein bands by polyanion precipitation and conversion of the turbidity units into cholesterol values.

However, this process is time consuming and necessitates the use of an electrophoresis apparatus, as well as of a densitometer, for the evaluation (Lab. Med., 1, 145/1977).

3. Determination of the LDL cholesterol value via the Friedewald formula (Clin. Chem., 18, 499/1972).

For the calculation of the LDL cholesterol value according to the Friedewald formula, the determination of 3 parameters is necessary: the cholesterol, HDL cholesterol and triglyceride values of the sample. The method is thus not sufficiently practicable. Furthermore, this approximation formula only applies to chylomicronfree samples and to samples with triglyceride values below 400 mg./dl.

4. Precipitation reactions

A process in which LDL is precipitated with the help of a lectin is described in Federal Republic of Germany Patent Specification No. 28 57 710. However, in the case of this method, the value for the LDL cholesterol can only be determined after redissolving the precipitate or only by difference formation of the cholesterol values before and after precipitation. This represents a considerable disadvantage.

A precipitation method for lipoproteins, in which LDL remains in the supernatant of the precipitation, is described in Federal Republic of Germany Patent Specification No. 26 00 664. However, this method is not sufficiently practicable for use in routine determinations since, for precipitating out of the lipoproteins, two working steps are necessary (addition of two different agents—polyethyleneimine and a cation exchanger—together with an intermediate incubation phase).

Therefore, there is a need for a simple process and reagent of high practicability and great accuracy for the determination of LDL lipoprotein.

Thus, according to the present invention, there is provided a process for the determination of low density lipoproteins (LDL) in body fluids, wherein high density lipoprotein (HDL) antibodies are added to a sample to be investigated, insolubles formed are separated off and the LDL or one of its components is determined in the supernatant.

The present invention is based upon the surprising ascertainment that, by the addition of HDL antibodies to the test sample, all lipoprotein fractions which disturb the LDL determination, i.e. not only HDL itself but especially VLDL and the chylomicrons, are precipitated out, whereas LDL itself is not affected by the precipitation. This is especially surprising since not only HDL but also LDL, VLDL and chylomicrons have a protein component which contains the same apolipoproteins even though in very different concentrations. Therefore, it could not have been foreseen that antibodies against HDL quantitatively precipitate out not only HDL but also VLDL and chylomicrons, without influencing LDL.*

*The precipitation of VLDL and chylomicrons can be accelerated by addition of well-known precipitating agents.

The LDL fraction remaining in the supernatant of the reagent can then be determined by the methods usual for this purpose. The determination of the bound cholesterol contained therein is preferably carried out with the use of the methods known for this purpose. Thus, the determination can be carried out, for example, by saponification with an alcoholic potassium hydroxide solution and chemical determination according to the Liebermann-Burchard method. Preferably, however, the determination is carried out enzymatically, using cholesterol oxidase and a cholesterol ester-splitting enzyme or enzyme system and especially cholesterol esterase. When using the latter method, there can be determined the amount of oxygen consumed, the amount of cholestenone formed or, most preferably, the amount of hydrogen peroxide formed, according to the methods known for this purpose. Since the determination of the bound cholesterol is well known, it is here not necessary to describe it in detail. However, it is to be pointed out that, in the scope of the process according to the present invention, due to the removal of the VLDL and chylomicron fractions, the appearance of turbidities is prevented, which could disturb an optical measurement of cholestenone or hydrogen peroxide when using colour reactions. Therefore, the process of the present invention is especially useful in conjunction with a colorimetric cholesterol determination method.

However, instead of determining the cholesterol contained in the LDL fraction or other LDL components, such as apolipoprotein B, phospholipids or triglycerides, it is also possible to determine the LDL fraction itself, using known methods. Thus, for example, there may be mentioned a nephelometric determination or the turbidimetric determination described in Federal Republic of Germany Patent Specification No. 30 07 764.

In the scope of the present invention, the HDL antibodies are used either in the form of an HDL antiserum, as defatted HDL antiserum or in the form of purified HDL antibody fractions. It is also possible to use HDL antibody fragments, for example Fab, $Fab_2$ and Fab' fragments. It is also possible to use antibodies against the apolipoproteins A, C and/or E of the HDL or their fragments. Finally, monoclonal HDL antibodies can also be employed.

The preparation of the antibodies used according to the present invention takes place with the use of pure HDL or of one of the said apolipoproteins as immunogen. For the obtaining of the antibodies, there can be employed the animal species conventionally used, sheep and rabbits being preferred. Apart from these animals or comparable animals, cell cultures can also be used for obtaining the antibodies.

The immune aggregate formed by the addition of the HDL antibodies can be separated off by conventional methods. If soluble HDL antibodies are used, then the separation preferably takes place by centrifuging. If immobilised, carrier-bound HDL antibodies are used, then the immune aggregate can be removed by simple separation of the liquid phase from the compact solid phase, for example a solid body coated with antibodies. If use is made of antibodies obtained with apolipoproteins as immunogen, then those are preferably used in which the apolipoprotein employed as immunogen has a lipid envelope. This can, for example, be achieved in that, after the usual delipidising and subsequent fractionation of the apolipoproteins, the selected apolipoprotein A, C and/or E fraction is again lipidised. However, as immunogen, it is preferable to use purified whole HDL fraction. Purification preferably takes place in known manner by isolation in an ultracentrifuge. In addition, a further purification can, if desired, be carried out by means of, for example, immobilised concavalin A using the methods of affinity chromatography or of electrophoresis. These methods are well-known and do not need to be described here in more detail.

The present invention also provides a reagent for the determination of the LDL fraction of body fluids which is characterised by a content of HDL antibodies. In a preferred embodiment, the reagent according to the present invention contains not only the above-mentioned HDL antibodies or the fragments or antibodies or fragments of HDL components described above in the explanation of the process but also a reagent for the determination of cholesterol.

A preferred reagent of the above-mentioned kind contains cholesterol oxidase, a cholesterol ester-splitting enzyme or enzyme system, a system for the determination of hydrogen peroxide and a surface-active agent.

According to a specially preferred embodiment of the above-mentioned reagent, it consists essentially of HDL antibodies, cholesterol oxidase, cholesterol esterase, peroxidase, 3,4-dichlorophenol, phenol, 4-aminophenazone, a non-ionic detergent, magnesium aspartate and a buffer (pH 7 to 8.5).

The reagent according to the present invention preferably contains the antibodies in the concentration of from $10^{-7}$ to $10^{-3}$ mol/l. (or kilo of solid body), referred to the determination solution. The antibody can be present in solid form and preferably in lyophilised form or in the form of a solution. The solvents used can be, for example, water, physiological saline, serum medium, a buffer, such as 0.01 to 0.5M tris buffer (pH 7 to 8.5) or 0.005 to 0.1M phosphate buffer (pH 6.5 to 8.5) optionally with the addition of sodium chloride in the amount present in physiological saline. If the antibodies are used in immobilised form, then examples of appropriate carrier substances include polysaccharides, such as cellulose, dextran, starch and the derivatives thereof, silicates, polyamides, collagen, latex, aluminium oxide, bovine serum albumin and similar carrier substances. The antibody can also be present bound on to the surface of test containers, such as synthetic resin test tubes.*

*Additionally, the reagent can contain well-known agents for the precipitation of VLDL and chylomicrons.

An important advantage of the process according to the present invention is the fact that, after the addition of a single reagent, all the lipoproteins, with the exception of LDL, can be removed from the sample and the diagnostically important LDL content or the cholesterol content of the LDL fraction is subsequently available for direct measurement without further pre-treatment of the sample. Furthermore, it is advantageous that the triglyceride-rich lipoproteins causing turbidities in the sample are removed so that, for the subsequent LDL or cholesterol determination, a clear sample is available.

The following Examples are given for the purpose of illustrating the present invention:

EXAMPLE 1

A) Preparation of purified HDL.

After the separation of VLDL and LDL in an ultracentrifuge, a narrowly selected HDL fraction (d 1.080 to 1.210) is isolated in an ultracentrifuge in the manner described by V. P. Skipski: Lipid composition of lipoproteins in normal and diseased states in: Blood Lipids and Lipoproteins: Quantitation, Composition and Metabolism, pub. Nelson, Wiley, N.Y., 1972, 471–583. The fraction is subsequently sedimented or floated twice at the densities 1.080 and 1.210.

The HDL fraction is purified by affinity chromatography over immobilised concanavalin A (Febs Lett., 91, 174–198/1974) or electrophoretically by means of Geon-Pevicon block electrophoresis according to R. W. Mahley, K. S. Holcombe (J. Lipid Res., 18, 314–324/1977 ).

B) Preparation of the antiserum. Animal species: sheep or rabbit

With the use of the immunogen obtained according to A, the following immunisation scheme is employed:

| day | administration | amount of immunogen |
|---|---|---|
| 0 | intradermally | 1 mg. protein (HDL) emulsified in Freund's adjuvant |
| 7 | intramuscularly | 1 mg. protein (HDL) emulsified in Freund's adjuvant |
| 14 | subcutaneously | 1 mg. protein (HDL) emulsified in Freund's adjuvant |
| 30 | intramuscularly | 1 mg. protein (HDL) emulsified in Freund's adjuvant |
| 60 | subcutaneously | 1 mg. protein (HDL) emulsified in Freund's adjuvant |
| every further 30 days | subcutaneously | 1 mg. protein (HDL) emulsified in Freund's adjuvant |

The first sample bleeding is carried out after 45 days.

C) 50 μl. of serum are mixed with 150 μl. of an antiserum prepared according to B. After incubating for 30 minutes at ambient temperature, the resultant precipitate is centrifuged off (2 minutes at 10,000 g ).

50 μl. of the clear precipitation supernatant are mixed with 2 ml. of a reagent which contains 0.1 mol/l. tris buffer (pH=7.7), 0.05 mol/l. magnesium aspartate, 1 mmol/l. 4-aminophenazone, 6 mmol/l. phenol, 4 mmol/l. 3,4-dichlorophenol, 0.3% fatty alcohol polyglycol ether, 400 U/l. cholesterol esterase, 250 U/l. cholesterol oxidase and 200 U/l. peroxidase.

After incubating for 20 minutes at ambient temperature, the extinction of the sample is measured against a reagent blank (the reagent blank contains 50 μl. of the antiserum and takes into account the cholesterol content of the antiserum).

$$\Delta E = \Delta E_{sample} - \Delta E_{reagent\ blank\ value}$$

$$LDL\ cholesterol\ (mg./dl.) = 1.385 \times \Delta E$$

| serum | appearance | cholesterol | triglycerides | NIH process+ | LDL cholesterol immunolog. precipitation |
|---|---|---|---|---|---|
| 1 | turbid | 353 mg/dl | 503 mg/dl | 234 mg/dl | 238 mg/dl |
| 2 | clear | 638 mg/dl | 591 mg/dl | 510 mg/dl | 495 mg/dl |
| 3 | clear | 350 mg/dl | 153 mg/dl | 237 mg/dl | 231 mg/dl |
| 4 | turbid | 195 mg/dl | 575 mg/dl | 102 mg/dl | 95 mg/dl |
| 5 | contains chylomicrons | 231 mg/dl | 379 mg/dl | 149 mg/dl | 130 mg/dl |

+The reference method used is the NIH process (after separating off VLDL and chylomicrons in an ultracentrifuge, LDL is precipitated. From the difference of the cholesterol values before and after precipitation, there is obtained the value for LDL cholesterol). Manual of Laboratory Operations, Lipid Research Clinics Program, Lipid and Lipoprotein Analysis, DHEW Publication No. 65-628.

EXAMPLE 2

A solution of 50 μl. each of VLDL, HDL, LDL and chylomicrons was mixed with 150 μl. of a rabbit antiserum which had been produced with HDL as immunogen. After centrifugation, the cholesterol content was determined in the supernatant in the manner described in Example 1.

| sample | cholesterol content of the sample | |
|---|---|---|
| | before precipitation | after precipitation |
| chylomicrons | 61.4 mg/dl | 2.6 mg/dl |
| VLDL | 23.2 mg/dl | 2.8 mg/dl |
| LDL | 177.0 mg/dl | 165.0 mg/dl |
| HDL | 50.9 mg/dl | 0.0 mg/dl |

We claim:

1. Method for determining low density lipoproteins or at least one component thereof in a body fluid sample which contains at least one additional lipoprotein fraction other than a low density lipoprotein fraction, said at least one additional lipoprotein fraction being selected from the group consisting of a high density lipoprotein fraction, a very low density lipoprotein fraction, and a chylomicron fraction, comprising:

(a) adding to said body fluid sample polyclonal antibodies produced by immunizing an animal with a member selected from the group consisting of high density lipoprotein, apolipoprotein A, apolipoprotein C, and apolipoprotein E, wherein said polyclonal antibodies bind to and precipitate any and all of (i) high density lipoproteins, (ii) very low density lipoproteins, and (iii) chylomicrons in said body fluid sample when contacted thereto, but do not precipitate low density lipoproteins, under conditions favoring binding and precipitating all of (i), (ii), and (iii) present in said body fluid sample, (b) separating any precipitate formed in (a) from said body fluid sample, and (c) determining low density lipoproteins or at least one component thereof in said body fluid sample.

2. The method of claim 1, wherein said polyclonal antibodies are obtained by immunizing said animal with high density lipoproteins.

3. The method of claim 1, wherein said polyclonal antibodies are obtained by immunizing said animal with apolipoprotein A.

4. The method of claim 1, wherein said polyclonal antibodies are obtained by immunizing said animal with apolipoprotein C.

5. The method of claim 1, wherein said sample contains all of low density lipoproteins, high density lipoproteins, very low density lipoproteins, and chylomicrons.

6. The method of claim 1, wherein said at least one component is cholesterol.

7. The method of claim 1, further comprising buffering said body fluid sample to a pH of from 6.5 to 8.5.

8. The method of claim 1, wherein said polyclonal antibodies comprise HDL specific antiserum.

9. The method of claim 8, wherein said HDL specific antiserum is defatted.

10. The method of claim 1, wherein said polyclonal antibodies are obtained by immunizing a sheep or rabbit.

11. The method of claim 1, wherein said polyclonal antibodies are immobilized on a solid phase.

12. The method of claim 1, wherein said polyclonal antibodies are obtained by immunizing a sheep or rabbit with high density lipoprotein intradermally, followed by an intramuscular injection seven days later, which is followed by a subcutaneous injection seven days later, which is in turn followed by an intramuscular injection sixteen days later, which is in turn followed by a subcutaneous injection 30 days later, each said injection comprising 1 mg of high density lipoprotein, wherein antibodies are collected from said sheep or rabbit no sooner than 45 days from said intradermal injection.

13. The method of claim 1, wherein said polyclonal antibodies bind to apolipoprotein A and apolipoprotein C.

14. The method of claim 13, wherein said polyclonal antibodies further comprise antibodies which bind to apolipoprotein E.

15. The method of claim 1, comprising separating any precipitate via centrifugation.

16. The method of claim 11, comprising separating said polyclonal antibodies immobilized on a solid phase, by centrifugation.

* * * * *